United States Patent
Horn et al.

(10) Patent No.: US 7,807,402 B2
(45) Date of Patent: Oct. 5, 2010

(54) REAGENT FOR FLUORIMETRIC DETERMINATION OF ANALYTES

(75) Inventors: Carina Horn, Alsbach-Haehnlein (DE); Hans-Peter Josel, Weilheim (DE); Juergen Spinke, Lorsch (DE); Rupert Herrmann, Weilheim (DE); Dieter Heindl, Paehl (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/107,116

(22) Filed: Apr. 22, 2008

(65) Prior Publication Data

US 2008/0305469 A1   Dec. 11, 2008

Related U.S. Application Data

(62) Division of application No. 10/766,457, filed on Jan. 28, 2004, now Pat. No. 7,378,255.

(30) Foreign Application Priority Data

Jan. 28, 2003   (DE) ................. 103 03 265

(51) Int. Cl.
    *C12Q 1/26* (2006.01)
(52) U.S. Cl. .............. 435/25; 436/172; 436/800; 436/904
(58) Field of Classification Search ............ 435/25, 435/7.9; 436/172, 800, 904
    See application file for complete search history.

(56) References Cited

U.S. PATENT DOCUMENTS

| | | | |
|---|---|---|---|
| 4,558,130 A | 12/1985 | Buckler et al. | |
| 4,656,141 A | 4/1987 | Birks et al. | |
| 5,445,944 A * | 8/1995 | Ullman | 435/28 |
| 5,795,729 A | 8/1998 | Lee | |
| 5,912,139 A | 6/1999 | Iwata et al. | |
| 6,468,753 B1 * | 10/2002 | Smith et al. | 435/6 |
| 7,332,354 B2 * | 2/2008 | Heindl et al. | 436/544 |
| 7,378,255 B2 * | 5/2008 | Horn et al. | 435/25 |
| 2003/0186349 A1 | 10/2003 | Makings | |

FOREIGN PATENT DOCUMENTS

| | | |
|---|---|---|
| EP | 0 190 740 B1 | 8/1986 |
| EP | 0 431 456 B1 | 11/1990 |
| EP | 0 441 222 A3 | 8/1991 |
| EP | 0 620 283 A1 | 3/1994 |
| EP | 0 574 769 B1 | 4/1996 |
| EP | 0 831 327 B1 | 9/1997 |
| JP | 63277680 | 11/1988 |
| WO | WO 91/09139 | 6/1991 |
| WO | WO 93/06487 | 4/1993 |

OTHER PUBLICATIONS

Song et al. Photophysical Properties of Polyads Containing a Fluorescein Moiety. Dyes and Pigments 42 (1999) 149-158.*
Zhang et al. Photoinduced Intramolecular Electron Transfer in an Anthraquinone-Fluorescein-Carbazole Model. J of Phtochemistry and Photobiology A Chemistry 103 (1997) 63-67.*
Haugland, R P, Chapter 10—Section 10.5: Substrates for Miscellaneous Enzymes, Handbook of Fluorescent Probes and Research Chemicals, 1996, 6th ed., Molecular Probes, pp. 236-237, Eugene, OR, USA.
Ryabov, A D, Firsova, Y N, Ershov, A Y, Dementiev, I A. Spectrophotometric kinetic study and analytical implications of the glucose oxidase-catalyzed reduction of $[M^{iii} (LL)_2 Cl_2]+$complexes by D-glocuse (M= Os and Ru, LL=2,2'—bipyridine and 1,10-phenanthroline type ligands), JBIC 1999, 4:175-182.
Woltman, S J, Even, W R, Weber, S G. "Chromatographic Detection Using Tris (2,2'—bipyridyl)ruthenium (III) as a Fluorogenic Electron- Transfer Reagent", Anal. Chem. 1999, 71, 1504-1512.
Haugland, R P, "Handbook of Fluorescent Probes and Research Chemicals", Molecular Probes, Sixth Edition, Chapter.10 —Section 10.5 Substrates for Miscellaneous Enzymes, pp. 236-237.
Borchardt, R T, Cohen, L A, "Stereopopulation Control. III. Facilitation of Intramolecular Conjugate Addition of the Carboxyl Group", Journal of the American Chemical Society, 94:26, Dec. 27, 1972, 9175-9182.
Song. A, Zhang, H, Zhang. M, Shen, T. "Photophysical properties of polyads containing a fluorescein moiety", Dyes and Pigments 42 (1999) 149-158.
Zhang, H, Zhang, M, Shen, T. "Photoinduced intramolecular electron transfer in an anthraquinone-fluorescein-carbazole model", Journal of Photochemistry and Photobiology A: Chemistry 103 (1997) 63-67.
Lakowicz, J.R., Chapters 13, 14 & 15, Principles of Fluorescence Spectroscopy, Kluwer Academic/Plenum Publishers, New York, NY 1999, pp. 367-443.

* cited by examiner

Primary Examiner—Ralph Gitomer
(74) Attorney, Agent, or Firm—McDonnell Boehnen Hulbert & Berghoff, LLP

(57) ABSTRACT

A method and reagent for detecting the presence or amount of an analyte by a redox reaction and a fluorimetric determination, is disclosed. The reagent comprises a compound of the general formula Q-F as a redox indicator, wherein Q is a quencher group and F is a fluorophore group. The quencher group Q or/and the fluorophore group F can be reduced or oxidized, and the fluorescence can change depending on the reduction or oxidation.

12 Claims, 1 Drawing Sheet

REAGENT FOR FLUORIMETRIC
DETERMINATION OF ANALYTES

PRIORITY CLAIM

This application is a division of U.S. patent application Ser. No. 10/766,457 (now U.S. Pat. No. 7,378,255 B2) filed 28 Jan. 2004, which claims priority under 35 U.S.C. §119 to German Application No. 103 03 265.7 filed 28 Jan. 2003.

DESCRIPTION

The invention concerns methods and reagent kits for the fluorimetric determination of analytes.

There are numerous methods for determining analytes for example for diagnostic applications. One approach is to determine the analyte by means of a redox reaction and a redox indicator. In this case an oxidizing or reducing system acts directly on the redox indicator or via a mediator. The presence of the analyte results in a reduction or oxidation of the redox indicator which allows a qualitative or quantitative determination.

Depending on the type of redox indicator, the indicator can be determined by a colorimetric, fluorimetric or electrochemical method of detection. Examples of colorimetric detection reagents are heteropoly acids (EP-B-0 431 456), tetrazolium compounds (EP-B-0 574 769), nitrosoaromatic compounds (EP-A-0 620 283), RIND compounds (EP-B-0 190 740), phenazines (WO 93/06487) and indanthrones (EP-B-0 831 327). Examples of electrochemical detection reagents are nitrosoaromatics, phenazines, potassium hexacyanoferrate and benzoquinone (cf. e.g. EP-A-0 441 222 and EP-A-0 505 494). Examples of fluorimetric detection reagents are resazurin (U.S. Pat. No. 5,912,139), transition metal complexes (Ryabov et al., JBIC 4 (1999), 175-182; Woltman et al., Anal. Chem. 71 (1999), 1504-1512) and scopoletin, esculetin, p-hydroxyphenylacetic acid, di-chlorofluorescein, N-acetyl-3,7-dihydroxyphenoxazine and MNBDH which are used exclusively to detect $H_2O_2$ (see also R. Haughland, Handbook of Fluorescent Probes and Research Chemicals, $6^{th}$ edition, 1996).

However, the fluorimetric detection reagents known from the prior art have some disadvantages. Thus most known fluorescent indicators require that metabolites such as glucose are determined by detecting $H_2O_2$ generated by glucose oxidase. This reaction usually has to be catalytically supported by the enzyme peroxidase and is very prone to interference by electron donors such as urea or bilirubin. The reagents are also not stable for long time periods.

In contrast redox indicators that allow an oxygen-independent detection of glucose, i.e. which directly accept an electron from an oxidizing enzyme instead of oxygen, are advantageous. However, only resazurin and Os and Ru complexes are known to be suitable electron acceptors for this. However, in the case of resazurin the emission bands of the resorufin formed by the redox reaction strongly overlap the absorption bands of non-reacted resazurin which considerably reduces the sensitivity of the analyte determination. As a result of their high redox potential (e.g. Ru complexes), the transition metal complexes exhibit a strong interference by compounds such as ascorbic acid. Their fluorescence efficiency also varies with the oxygen content of the sample.

Furthermore with the previously known fluorescent indicators the excitation light sources used are mainly limited to the UV and green range of light. Thus for example an inadequate number of compounds are known which allow use of the particularly strong blue and red LEDs.

Hence an object of the present invention was to provide new redox-active compounds as detection reagents for the fluorimetric determination of analytes which can at least partially eliminate the disadvantages of the prior art.

This object is achieved according to the invention by providing intramolecular conjugates of fluorophores and quenchers as redox indicators whose fluorescence can be changed by the redox reaction. In particular the use of conjugates which contain reducible or oxidizable quenchers enables of universal redox indicators to be provided that allow the use of any desired excitation light sources depending on the choice of the fluorophore group. This basic principle of the present invention was exemplified using a quinone-fluorescein conjugate as a redox indicator for the fluorimetric determination of glucose. The quinone group of the conjugate is a quencher group which suppresses the fluorescence of the fluorophore group fluorescein. This quenching effect is abolished when the quinone is enzymatically reduced to dihydroquinone such that the fluorescence of the redox indicator increases depending on the extent of the redox reaction. Conjugates containing other quencher groups and fluorophore groups can be used correspondingly. All molecules come into consideration as quencher groups which partially reduce or completely quench the fluorescence intensity or fluorescence lifetime of the specially selected fluorophore group as a result of a molecular interaction. Examples of the processes that are the basis for the molecular interaction are dynamic quenching, static quenching, complex formation, electron transfer, energy transfer, charge transfer, photon-induced electron transfer (PET) and photon-induced charge transfer (PCT). Thus a quencher group may also be an acceptor group whose absorption bands in its oxidized or reduced state overlap the emission bands of the fluorophore (donor) and partially or completely reduces the fluorescence intensity or fluorescence lifetime of the fluorophore group (donor) due to a dipole-dipole interaction (so-called fluorescence resonance energy transfer (FRET) (cf. also: J. R. Lakowicz, Principles of Fluorescence Spectroscopy, Kluwer Academic/Plenum Publishers, New York, 1999).

Hence a first aspect of the present invention is a method for detecting an analyte by a redox reaction and a fluorimetric determination, characterized in that a sample containing the analyte is contacted with a detection reagent which contains a compound of the general formula (I) as the fluorimetric redox indicator:

wherein Q is a quencher group and F is a fluorophore group. Such compounds are in principle already described in the prior art (cf. for example Zhang et al., Journal of Photochemistry and Photobiology A: Chemistry 103 (1997), 63-67; Song et al., Dyes and Pigments 42 (1999), 149-158).

Another aspect of the invention is a reagent for detecting an analyte by a redox reaction and a fluorimetric determination which contains a compound of the general formula (I) as described above as the fluorimetric redox indicator.

The present invention is suitable for detecting any analytes that can be determined by a redox reaction. The detection can be qualitative, semi-quantitative or quantitative. In one embodiment of the invention the analyte can be a reducible or oxidizable substance, for example a metabolite present in a body fluid such as blood, serum, plasma, urine etc. In this case it is expedient to use a detection reagent which, in addition to the redox indicator, also contains one or more enzymes for reducing or oxidizing the analyte and optionally coenzymes such as nicotine nucleoside derivatives e.g. $NAD^+$, $NADP^+$ or flavin nucleoside derivatives e.g. FAD. Preferred examples of such analytes are glucose, lactate, alcohol, galactose, cholesterol, fructose, phenylalanine, alanine, leucine, glycerol, pyruvate and creatinine. Glucose can for example be detected by known methods using glucose oxidase or glucose dehydrogenase/diaphorase.

Furthermore the analyte may also be an enzyme that catalyses a redox reaction for example an oxidoreductase such as glucose oxidase (GOD), glucose dye oxidoreductase (Gluc-DOR), dehydrogenase or an enzyme whose reaction can be coupled to an oxidoreductase reaction such as glutamate-oxaloacetate transferase (GOT).

In addition to the redox indicator and, if required, an enzyme for reducing or oxidizing the analyte, the detection reagent can additionally contain common components such as coenzymes, auxiliary substances, enzyme cascades, buffers and optionally mediators. Substances are suitable as mediators which support the acceptance or release of electrons by the redox indicator (I). However, in general those redox indicators (I) are preferred which can directly accept or release electrons.

The method according to the invention is carried out in conventional test formats such as in dry or wet tests. In a dry test an absorbent material e.g. in the form of a test strip is used as a support on which the detection reagent can be applied in a dry form e.g. as a lyophilisate. Liquid tests are carried out in a liquid phase in suitable reaction vessels e.g. cuvettes, microtitre plates etc. where the detection reagent can be provided in the reaction vessel itself or in separate containers in a dry or liquid form.

For the fluorimetric determination, the sample is irradiated with excitation light of a predetermined wavelength and the fluorescence emission light emitted by the sample that has a different wavelength is determined by known methods. The free selection of fluorophores enables the present invention to provide optimized test formats for the determination of any analytes.

The fluorescence activity of the redox indicator (I) according to the invention differs depending on whether the compound is present in an oxidized or reduced state. The quencher group Q is preferably a group that can be reduced or oxidized by the redox reaction and whose quencher activity, i.e. its ability to at least partially quench the fluorescence of a neighbouring fluorophore group, changes as a function of the redox state. In contrast, the fluorophore group F is preferably a group that cannot be reduced or oxidized by the redox reaction.

The quencher group is preferably covalently coupled to the fluorophore group. The coupling may be direct or via a linker. Suitable linkers are known linear or branched linker groups e.g. alkylene groups which optionally contain heteroatoms such as O, N or S, or peptides. The chain length of the linker is preferably 1-20 atoms.

The difference in the fluorescence intensity of the redox indicator in the quenched and unquenched state is preferably between 5% and 100%. However, it is not necessary for the fluorescence to be completely suppressed in the quenched state since the residual fluorescence can be used for calibration purposes.

The quencher group Q can be a reducible group in which case the quencher activity can be increased or decreased by reduction. The quencher activity is preferably decreased by reduction. Preferred examples of reducible quencher groups are quinones, aromatic nitroso compounds such as nitrosoanilines and other nitrosobenzene derivatives, N-oxides and especially N-oxides in which the nitrogen atom of the N-oxide group is a component of an aromatic ring system, benzofurans, nitrosonaphthalimides, so-called spin labels, tetrazolium compounds, phenazines, pyridines, anthraquinones, quinoxalines, pyrimidoquinones, phenylhydroxylamines, indanthrones, phenathrenquinones and organic metal complexes.

Alternatively the quencher group Q can be an oxidizable group in which case its quencher activity can be increased or decreased by oxidation. The quencher activity is preferably increased by oxidation. Examples of oxidizable quencher groups are hydroquinones, phenylenediamines, dihydrophenazines, dihydronaphthoquinones, dihydroanthraquinones and organic metal complexes.

As already stated the fluorophore group F is preferably a group that cannot be reduced or oxidized by the redox reaction. This allows F to be selected from a very wide range of known fluorophore groups. Preferred examples of fluorophore groups are fluorescein and fluorescein derivatives, rhodamines, tetramethylrhodamines, coumarins, resorufins, pyrenes, anthracenes, phenylenes, phthalocyanines, cyanines, xanthenes, amidopyrylium dyes, oxazines, quadrain dyes, carbopyronines, NBD derivatives, BODIPY™ fluorophores (from Molecular Probes Inc.), ALEXA™ fluorophores (from Molecular Probes Inc.), lanthanide chelates, metalloporphyrins, NIR fluorophores, rhodol dyes, naphthalimides and porphyrins. Fluorophores that can be excited by blue light or red light are particularly preferred.

Another aspect of the invention is a reagent for detecting an analyte by a redox reaction and a fluorimetric determination comprising a compound of the general formula (I) as a redox indicator:

a. Q-F  (I)

wherein Q is a quencher group and F is a fluorophore group, and wherein the quencher group Q or/and the fluorophore group F can be reduced or oxidized and the fluorescence can change depending on the reduction or oxidation.

In addition to the redox indicator the reagent according to the invention can also contain other components selected from enzymes, coenzymes, auxiliary substances, buffers and mediators.

The present invention is further elucidated by the following figures and the example.

DETAILED DESCRIPTION OF THE DRAWINGS

EXAMPLES

Example 1

Figure 1:
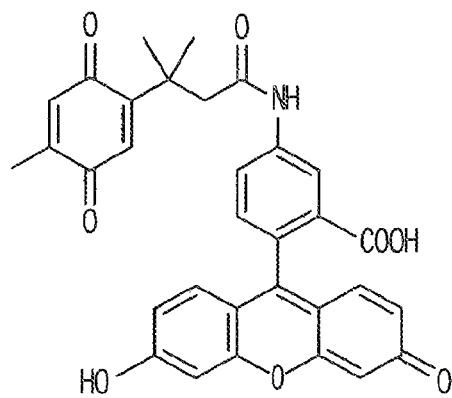
FIG. 1 shows a quinone-fluorescein conjugate as an example of a redox indicator according to the invention.

Synthesis of a Quinone-fluorescein Derivative (FIG. 1)

The quinone derivative 2-methylquinone-3,3-dimethylpropionic acid is synthesized according to Borchardt et al., J. Amer. Chem. Soc. (1972) 94 (26), 9175-9182.

For the reaction 93 mg triphosgene (Merck Cat. No. 814283) is dissolved in 6 ml tetrahydrofuran and 70 µl dimethylformamide is added under inert conditions and while cooling on ice. 312 mg 5-aminofluorescein (Fluka Cat. No. 07980), 200 mg quinone derivative and 375 µl triethylamine are added.

After appropriate reaction, the product mixture is taken up in ice water and extracted several times with ethyl acetate. The combined ester phases are extracted with water and subsequently dried over calcium chloride.

It is purified further by means of preparative HPLC.

Yield 70 mg; mass spectrum corresponds to theory.

Example 2

Glucose Determination with a Quinone-fluorescein Derivative as the Redox Indicator Reaction scheme:

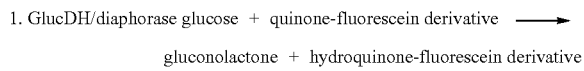

1. GlucDH/diaphorase glucose + quinone-fluorescein derivative ⟶ gluconolactone + hydroquinone-fluorescein derivative The following compounds were added to a 3 ml fluorescence cuvette (the stated concentrations refer to the final concentration in the cuvette):

| | |
|---|---|
| glucose dehydrogenase (GlucDH): | 1.3 U/ml |
| diaphorase: | 1.3 U/ml |
| NAD⁺: | 36.9 μmol/l |
| quinone-fluorescein (FIG. 1; from example 1): | 35.4 μmol/l |

Figure 2:
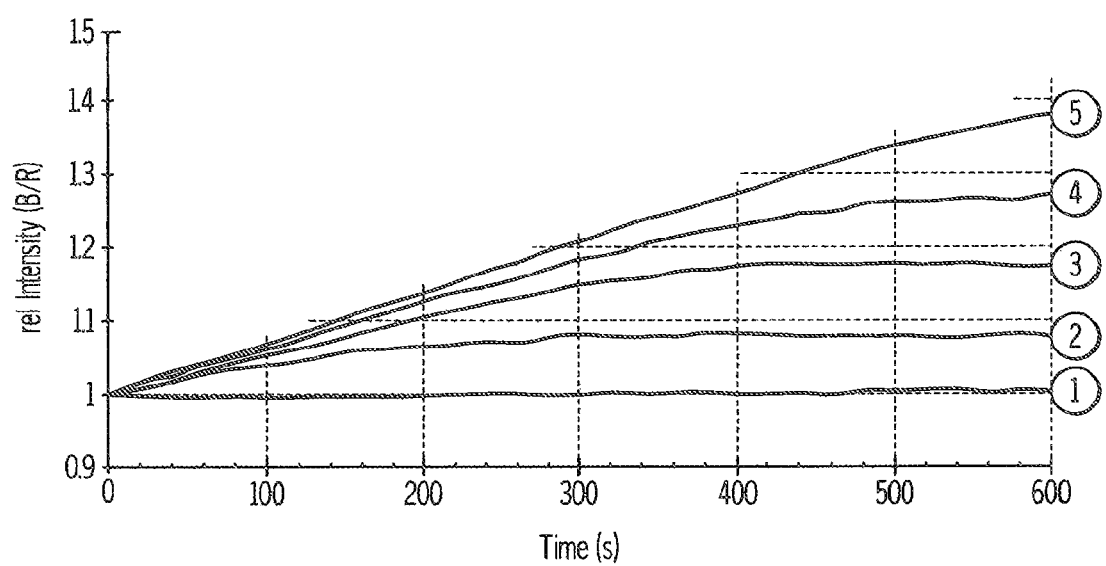
FIG. 2 shows the kinetics of quinone-fluorescein reduction in a system for detecting glucose at various glucose concentrations.

The reaction is started by adding an aqueous glucose solution (0.1 M phosphate buffer, pH 7.4 containing 1% NaCl). The kinetics of the reaction were recorded for various glucose concentrations at an excitation wavelength of 470 nm and an emission wavelength of 525 nm. The result of the experiment is shown in FIG. 2. The curves numbered 1, 2, 3, 4 and 5 correspond to glucose concentrations of 0 mg/dl, 4 mg/dl, 6 mg/dl, 7 mg/dl and 8 mg/dl and the relative intensities are plotted versus time in seconds.

FIG. 2 shows that an increase in fluorescence is found which is proportional to the glucose concentration present in the sample.

What is claimed is:

1. A reagent for detecting the presence or amount of an analyte by a redox reaction and a fluorimetric determination comprising:
    a compound of the general formula Q-F as a redox indicator, wherein Q is a quencher group and F is a fluorophore group, the quencher group Q can be reduced or oxidized by said redox reaction, and the fluorescence activity of said Q-F compound can change depending on if said quencher group of said Q-F compound is present in a reduced or oxidized state; and
    an enzyme for reducing or oxidizing the analyte and optionally a coenzyme.

2. The reagent of claim 1, wherein Q is a reducible group.

3. The reagent of claim 2, wherein Q is selected from the group consisting of quinones, aromatic nitroso compounds, nitrosoanilines, nitrosobenzene derivatives, N-oxides, N-oxides in which the nitrogen atom of the N-oxide group is a component of an aromatic ring system, benzofurans, nitrosonaphthalimides, spin labels, tetrazolium compounds, phenazines, pyridines, anthraquinones, quinoxalines, pyrimidoquinones, phenylhydroxylamines, indanthrones, phenanthrenequinones and organic metal complexes.

4. The reagent of claim 1, wherein Q is an oxidizable group.

5. The reagent of claim 4, wherein Q is selected from the group consisting of hydroquinones, phenylenediamines, dihydrophenazines, dihydronaphthoquinones, dihydroanthraquinones and organic metal complexes.

6. The reagent of claim 1, wherein F is a group that cannot be reduced or oxidized by the redox reaction.

7. The reagent of claim 6, wherein F is selected from the group consisting of fluorescein, fluorescein derivatives, rhodamines, tetramethylrhodamines, coumarins, resorufins, pyrenes, anthracenes, phenylenes, phthalocyanines, cyanines, xanthenes, amidopyrylium dyes, oxazines, quadrain dyes, carbopyronines, NBD derivatives, BODIPY fluorophores, ALEXA fluorophores, lanthanide chelates, metalloporphyrins, NIR fluorophores, rhodol dyes, naphthalimides and porphyrins.

8. The reagent of claim 1, wherein Q is bound to F by a linker.

9. The reagent of claim 8, wherein the linker has a chain length of 1-20 atoms.

10. The reagent of claim 1, wherein the redox indicator can directly accept or release electrons.

11. The reagent of claim 1, wherein the redox indicator can accept or release electrons via a mediator.

12. The reagent of claim 1 further comprising other components selected from enzymes, coenzymes, additives, buffers and mediators.

* * * * *